(12) United States Patent
Wooton et al.

(10) Patent No.: US 7,049,831 B2
(45) Date of Patent: May 23, 2006

(54) FLUID QUALITY CONTROL USING BROAD SPECTRUM IMPEDANCE SPECTROSCOPY

(75) Inventors: David Lee Wooton, Beaverdam, VA (US); Richard Walter Hirthe, Milwaukee, WI (US); Martin Arthur Seitz, Brookfield, WI (US)

(73) Assignee: Eaton Corporation, Cleveland, OH (US)

(*) Notice: Subject to any disclaimer, the term of this patent is extended or adjusted under 35 U.S.C. 154(b) by 0 days.

(21) Appl. No.: 10/778,896

(22) Filed: Feb. 16, 2004

(65) Prior Publication Data

US 2005/0179449 A1 Aug. 18, 2005

(51) Int. Cl.
*G01R 27/08* (2006.01)
*G01R 23/16* (2006.01)

(52) U.S. Cl. ............... 324/698; 324/76.22; 702/84
(58) Field of Classification Search ........... 324/698, 324/691, 76.22; 702/25, 76, 81–84; 73/53.01, 73/53.05; 436/150
See application file for complete search history.

(56) References Cited

U.S. PATENT DOCUMENTS

| | | | |
|---|---|---|---|
| 4,686,857 A * | 8/1987 | Kato .................. 73/304 R |
| 5,361,628 A | 11/1994 | Marko et al. ............. 73/116 |
| 5,660,181 A | 8/1997 | Ho et al. ................ 600/408 |
| 5,985,120 A | 11/1999 | Cholli et al. ............. 204/452 |
| 6,245,571 B1 | 6/2001 | Roman |
| 6,278,281 B1 | 8/2001 | Bauer et al. ............. 324/441 |
| 6,369,579 B1 * | 4/2002 | Riegel .................... 324/439 |
| 6,377,052 B1 | 4/2002 | McGinnis et al. ........ 324/446 |
| 6,380,746 B1 | 4/2002 | Polczynski et al. ....... 324/446 |
| 6,433,560 B1 | 8/2002 | Hansen et al. .......... 324/668 |
| 6,549,861 B1 | 4/2003 | Mark et al. ............. 702/76 |
| 6,560,352 B1 | 5/2003 | Rowe et al. ............. 382/115 |
| 6,620,621 B1 | 9/2003 | Cohenford et al. ........ 436/63 |
| 6,735,541 B1 * | 5/2004 | Kern et al. .............. 702/84 |
| 6,820,012 B1 * | 11/2004 | Sunshine ................ 702/22 |
| 6,844,745 B1 * | 1/2005 | Schachameyer et al. ... 324/698 |
| 6,850,865 B1 * | 2/2005 | Hirthe et al. ............ 702/181 |

(Continued)

FOREIGN PATENT DOCUMENTS

EP 1 098 196 A2 5/2001

(Continued)

OTHER PUBLICATIONS

U.S. Appl. No. 10/793,344, filed Mar. 4, 2004, Hirthe et al.

(Continued)

*Primary Examiner*—Anjan Deb
(74) *Attorney, Agent, or Firm*—Jaquez & Associates; Martin J. Jaquez, Esq.; Larry D. Flesner

(57) ABSTRACT

A system and method for monitoring and controlling the properties of fluids is disclosed. The inventive concept employs impedance spectroscopy (IS) measurements, and is suitable for real-time, in situ, monitoring and quality control operations, such as quality control during the manufacture of blended lubricants. IS data are obtained for three or more frequencies, where the lowest frequency is less than 1 Hz and the highest frequency is greater than 1 Hz. These data may be interpreted according to statistical techniques such as Principal Component Regression, analytical techniques such as equivalent circuit modeling, or by a combination thereof. The data analysis provides characteristics, or IS signatures, relating to the properties of the fluid. IS signatures for a test fluid are compared to IS signatures for calibration fluids to determine whether the properties of the test fluid fall within specified limits. Quality control adjustments to the test fluid properties may be performed based on the IS signatures.

55 Claims, 15 Drawing Sheets

U.S. PATENT DOCUMENTS

| | | | |
|---|---|---|---|
| 2002/0125899 A1* | 9/2002 | Lvovich et al. | 324/698 |
| 2003/0141882 A1 | 7/2003 | Zou et al. | 324/698 |
| 2003/0222656 A1* | 12/2003 | Phillips et al. | 324/605 |
| 2004/0197927 A1* | 10/2004 | Jeng et al. | 436/171 |
| 2004/0239344 A1* | 12/2004 | Hu | 324/698 |
| 2005/0110503 A1* | 5/2005 | Koehler et al. | 324/710 |

FOREIGN PATENT DOCUMENTS

| | | |
|---|---|---|
| WO | WO 03/014729 A1 | 2/2003 |
| WO | WO 03/104798 A1 | 12/2003 |

OTHER PUBLICATIONS

Jianxun Hu, M.S., "The Characterization of Lubricating Fluids Using AC Impedance Spectroscopy", a dissertation, Apr. 23, 2004, Marquette University Library, Milwaukee, WI.

"Principal Components Analysis" (downloaded on Nov. 25, 2003) from http://www.okstate.edu/artsci/botany/ordinate/PCA.htm.

Aapo Hyvarinen, "Principal Component Analysis", Apr. 23, 1999 (downloaded on Nov. 4, 2003) from http://www.cis.hut.fi/~aapo/papers/NCS99web/node5.html.

Jaakko Hollmen, "Principal Component Analysis", Mar. 8, 1996 (downloaded on Nov. 4, 2003) from http://www.cis.hut.fi/~jhollmen/dippa/node30.html.

"Principal Component Analysis" (downloaded on Nov. 4, 2003) from http://www.casaxps.cwc.net/FactorAnalysis.htm.

"Principal Components and Factor Analysis" (downloaded Nov. 4, 2003) from http://www.statsoftinc.com/textbook/stfacan.html.

"Algorithms, The Beer Lambert Law" (downloaded on Nov. 26, 2003) from http://www.galactic.com/algorithms/beer_lambert.htm.

"Algorithms, Classical Least Squares (CLS)" (downloaded on Nov. 26, 2003) from http://www.galactic.com/algorithms/cls.htm.

"Algorithms, Discriminant Analysis, The Mahalanobis Distance" (downloaded on Nov. 25, 2003) from http://www.galactic.com/algorithms/discrim_mahaldist.htm.

"Algorithms, Discriminant Analysis, The PCA/MDR Method" (downloaded on Nov. 25, 2003) from http://www.galactic.com/algorithms/discrim_pca.htm.

"Algorithms, Inverse Least Squares" (downloaded on Nov. 25, 2003) from http://www.galactic.com/algorithms/ils.htm.

"Algorithms, Least Squares Regression" (downloaded on Nov. 25, 2003) from http://www.galactic.com/algorithms/least_squares.htm.

"Algorithms, Partial Least Squares" (downloaded on Nov. 25, 2003) from http://www.galactic.com/algorithms/pls.htm.

"Algorithms, Principal Component Analysis Methods" (downloaded on Nov. 25, 2003) from http://www.galactic.com/algorithms/pca.htm.

"Algorithms, Principal Component Regression" (downloaded on Nov. 26, 2003) from http://www.galactic.com/algorithms/pcr.htm.

Wang, et al. "The application of a.c. impedance technique for detecting glycol contamination in engine oil", Sensors and Actuators B, Elsevier Sequoia S.A., Lausanne, CH, vol. 40, No. 2-3 May 15, 1997, pp. 193-197.

Australian Coal Research Limited "Online Monitoring of Lubrication Oil Contamination and Degradation", "Online!", Apr. 30, 2002, XP002329440.

Seitz, M.A., et al., "Process-Monitoring Via Impedance Spectroscopy", Materials Research Society Symposium Proceedings, Materials Research Society, Pittsburg, PA; 1996, pp. 57-68.

* cited by examiner

For the chosen data basis the following GMDH model for Ca was generated:

X3 = (1.897 e+2) z22 + (1.252 e+1) z21 z22 + 5.258e+3 z21 = (4.852 e-6) X10 + 8.002
z22 = (-0.5437) z11² - (0.4926) z12² + (0.8374) z12 - (1.848) z11 z12 - (0.9418) z11
z11 = (2.946 e-6) X6 - 18.49
z12 = (-3.041 e-10) z5² + (6.547 e-11) z8² + (2.142 e-3) X5 + (2.359 e-4) X8 - (3.563 e+3)

Prediction Error Sum Of Squares (PESS): ------ 0.0252
Mean Absolute Percentage Error: ------ 0.37 %
Approximation Error Variance: ------ 0.0197
Coefficient Of Determination (R-squared): ------ 0.9803

OUTPUT VARIABLE:
X3 - Ca (predicted)

RELEVANT INPUT VARIABLES: 4

X10 - 63 mHz reactance
X6 - 100 mHz resistive
X5 - 316 Hz resistive
X8 - 316 Hz reactance

Figure 7

For the chosen data basis the following MLR model for $CO_3$ was generated:

$Y = 9.00027 - (3.51383\ e\text{-}6)\ x1 + (2.01358\ e\text{-}6)\ x2 + (8.1867\ e\text{-}6)\ x3 - (8.4277\ e\text{-}7)\ x4 - (6.28198\ e\text{-}6)\ x5 - (2.92438\ e\text{-}6)\ x6 + (7.35774\ e\text{-}7)\ x7 + (2.6575\ e\text{-}7)\ x8 - (8.9446\ e\text{-}7)\ x9 - (6.99863\ e\text{-}7)\ x10$ Coefficient Of Determination (R-squared): ----- 0.9505

OUTPUT VARIABLE: Y - $CO_3$ (predicted)

INPUT VARIABLES: 10 x1 - 398 Hz resistive       x7 - 100 mHz resistive
x2 - 398 Hz reactance       x8 - 100 mHz reactance
x3 - 251 mHz resistive      x9 - 10 mHz resistive
x4 - 251 mHz reactance      x10 - 10 mHz reactance
x5 - 158 mHz resistive
x6 - 158 mHz reactance

Figure 10

FLUID QUALITY CONTROL USING BROAD SPECTRUM IMPEDANCE SPECTROSCOPY

CROSS REFERENCE TO RELATED APPLICATION

This application is related to the co-pending U.S. patent application, application Ser. No. 10/723,624, filed Nov. 26, 2003, titled "FLUID CONDITION MONITORING USING BROAD SPECTRUM IMPEDANCE SPECTROSCOPY" (Eaton Ref. No. 03-ASD-255(SR)). This application is commonly owned by the assignee hereof, and is hereby fully incorporated by reference herein as though set forth in full, for teachings on statistical techniques for use in performing analysis of Impedance Spectroscopy data, and is also provided in full in Appendix A of the present application.

BACKGROUND

1. Field

The present invention relates to methods and apparatus for monitoring and controlling the properties of fluids, and more particularly to a method and apparatus for quality control of fluids during manufacturing processes.

2. Description of Related Art

When manufacturing lubricating fluids blended with additives, analytical testing is required to verify that the properties of the blended lubricant are within defined specifications. The blending operation, in some exemplary approaches, may be performed in a tank or by in-line blending processes. Typical analytical tests, such as Fourier Transform Infrared (FT-IR) spectroscopy, kinematic viscosity as per ASTM D-445 or metal analyses—inductively coupled plasma spectrometry (ICP) as per ASTM D-5185, are performed on samples in a laboratory. Depending on laboratory operations and conditions, tests may require more than an hour for completion, and the blending process is typically suspended until satisfactory results are obtained. The delays may be extended if the results are unsatisfactory.

Systems for in-situ (e.g., performed in an operating system, such as an engine or transmission) monitoring of lubricating fluids are known. One such system is disclosed in U.S. Pat. No. 6,278,281 entitled "Fluid Control Monitor" issued to Bauer, et al. This patent describes a technique employing AC electro-impedance spectroscopy (referred to hereinafter as impedance spectroscopy or "IS"), and is implemented by means of probe electrodes placed in contact with the fluid to be tested. The method of operation includes making IS measurements at a first frequency that is less than 1 Hz and a second frequency that is greater than 1 Hz, comparing the two IS measurements, and declaring a "pass" or "fail" condition based on a previously determined empirical relationship.

However, this prior art lubricating fluid monitoring system effectively analyzes only a single characteristic of the IS spectra based on the difference of two IS measurements. Consequently, it is not capable of determining the complex properties of compound fluids, as is required when performing quality control measurements of fluids having a plurality of additives. Thus, a need exists for a real-time, in situ monitoring system for quality control of fluids during manufacturing operations.

SUMMARY

A system and method for monitoring and controlling the properties of fluids is disclosed. The inventive concept employs impedance spectroscopy (IS) measurements performed at three or more frequencies, and is suitable for real-time, in situ, measurements and quality control operations, such as monitoring and providing quality control during the manufacture of blended lubricants.

In one exemplary embodiment, IS measurements are made using probe electrodes in contact with a fluid. IS data are obtained for three or more frequencies, wherein the lowest frequency is less than 1 Hz, and the highest frequency is greater than 1 Hz. These IS data may be analyzed using statistical techniques, such as Principal Component Regression, or using analytical techniques, such as equivalent circuit modeling, or using a combination of such statistical and analytical techniques. The data analysis provides characteristics, or IS signatures, relating to the properties of the fluid. IS signatures for test fluids are compared to IS signatures for calibration fluids in order to determine whether the properties of the test fluids are within specified limits. Quality control adjustments to the test fluid properties may be performed based on the IS signatures.

BRIEF DESCRIPTION OF THE DRAWINGS

FIG. 7 is a Group Method For Data Handling model for impedance spectroscopy copy data relating to Ca concentration for exemplary calibration fluids.

FIG. 10 is a Multiple Linear Regression model for impedance spectroscopy data relating to $CO_3$ concentration for exemplary calibration fluids.

DETAILED DESCRIPTION

Throughout this description, embodiments and variations are described for the purpose of illustrating uses and implementations of the inventive concept. The illustrative description should be understood as presenting examples of the inventive concept, rather than as limiting the scope of the concept as disclosed herein.

Figure 1:
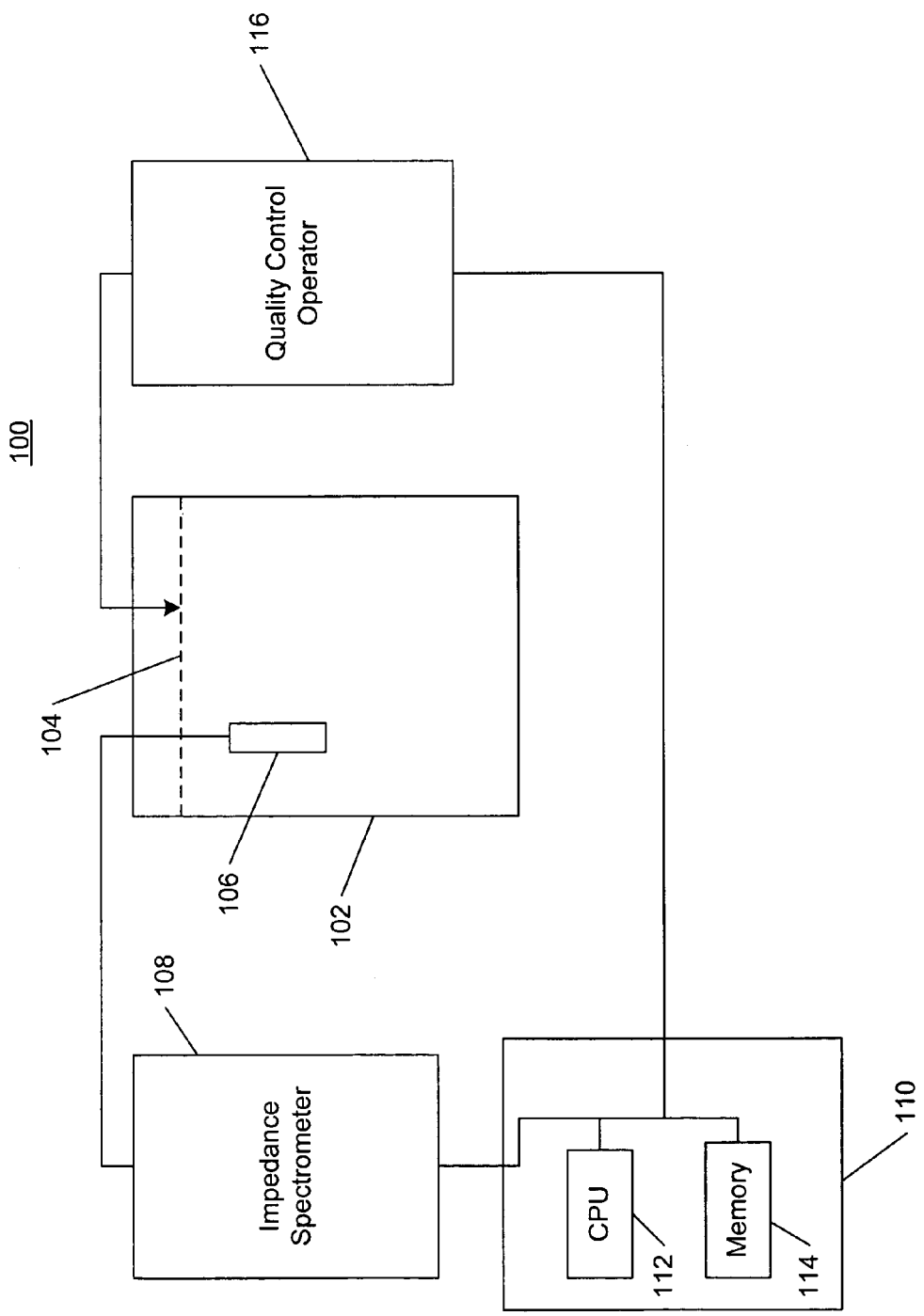
FIG. 1 is a block diagram of a simplified quality control system for fluids based on impedance spectroscopy.

FIG. 1 shows a block diagram of a simplified quality control system 100 for fluids based on IS measurements and analysis. A fluid container 102 may be a tank or an in-line container, such as a pipe. The container 102 contains a fluid 104, such as a blended lubricant, for which it is desired to monitor and control the properties of during a manufacturing process. For lubricant blending operations, the fluid 104 is typically maintained at a constant temperature (e.g., 60° Celsius) by a temperature controller (not shown). In another aspect of the inventive concept, the fluid container 102 may contain a fluid 104 that is a sample of a manufactured product to be tested for authenticity. In this aspect, the inventive concept detects counterfeit products, such as lubricants, that may have been substituted for a genuine product. In yet another embodiment, the fluid 104 may be a sample of a received product to be tested for quality.

An IS probe 106 is in contact with the fluid 104. Many suitable IS probes are known to those skilled in the electrochemical arts. U.S. Pat. No. 6,278,281 entitled "Fluid Control Monitor" issued to Bauer, et al., on Aug. 21, 2001, describes a plurality of suitable electrode probes that may be used in conjunction with the present invention. An exemplary IS probe device design utilizing concentric tubular electrodes, is disclosed in U.S. patent application No. 2003/0141882, Ser. No. 10/060,107, filed Jan. 31, 2002, titled "Probe Assembly for a Fluid Condition Monitor and Method of Making Same." Both the issued patent and the patent application cited above are commonly owned by the assignee hereof, and both are hereby fully incorporated by reference herein as though set forth in full, for their teachings on IS probe devices, and for their teachings on methods and equipment relating to IS measurements of fluids.

As shown in FIG. 1, the IS probe 106 is operatively connected to an impedance spectrometer 108. The construction and operation of impedance spectrometers are well known to persons skilled in the electrochemical arts, and commercial impedance spectrometers are available. IS instrumentation generally comprises an array of impedance and frequency response analyzers, as well as "lock-in" amplifiers. The equipment provides a source of AC signals of varying frequency. The IS equipment also provides circuitry for detecting the magnitude of electric current conducted through the sample. An exemplary combination of IS instrumentation may include an EG&G Potentiostat/Galvanostat Model 283 (EG&G is a Division of URS Corporation, of San Francisco, Calif.), and a Solartron Impedance/Gain-Phase Analyzer Model 1260 (hereinafter, Solartron 1260—Solartron Analytical is a member of the Roxboro Group plc, of Cambridge, United Kingdom). The Solartron 1260 provides an AC signal of varying frequency. Signal levels ranging from 125 mV in fully formulated lubricating fluids to 1000 mV in the base fluid have been found to provide well-defined IS data. The impedance spectrometer 108 is operatively coupled to a data processing system 110. In one embodiment, the data processing system 110 comprises a personal computer (PC). IS data acquisition may be accomplished using commercial PC-based computer programs such as "Z-Plot™", and "Z-View™" (see, for example, the operating manual titled "Zplot for Windows," Scribner Associates, Inc., version 2.1, 1998), as well as other software that may be custom-developed by persons skilled in the arts of scientific data acquisition. These PC-based computer programs for IS data acquisition are well known in the art.

As shown in FIG. 1, in one embodiment, the data processing system 110 includes a central processing unit (CPU) 112 and a memory 114, both of which are operatively connected to receive data from the impedance spectrometer 108, and operatively configured to output data to a quality control operator 116. The memory 114 stores software instructions used for acquiring data. The memory 114 also is used to store calibration data and software for data analysis. These functions are described more fully hereinbelow.

The quality control operator 116 may comprise a person, an apparatus, an automatic system, or a combination thereof. The results of IS data analyses performed by the data processor 110 are output to the operator 116, and the operator 116 may perform adjustments to the properties of the fluid 104 according to identified characteristics (e.g., IS signatures) of the IS spectra of the fluid 104 under study. For example, if the fluid 104 comprises a blended lubricant, and the IS signatures of the fluid 104 indicate that additive concentrations are beyond specified limits, the operator 116 may adjust a blending operation within the container 102 to bring the fluid properties within specifications. According to this example, persons skilled in the arts of manufacturing blended lubricants will readily understand the operations that may be performed by the operator 116. Exemplary methods for IS data analysis and determination of IS signatures are described in more detail hereinbelow.

Exemplary Data

Figure 2:
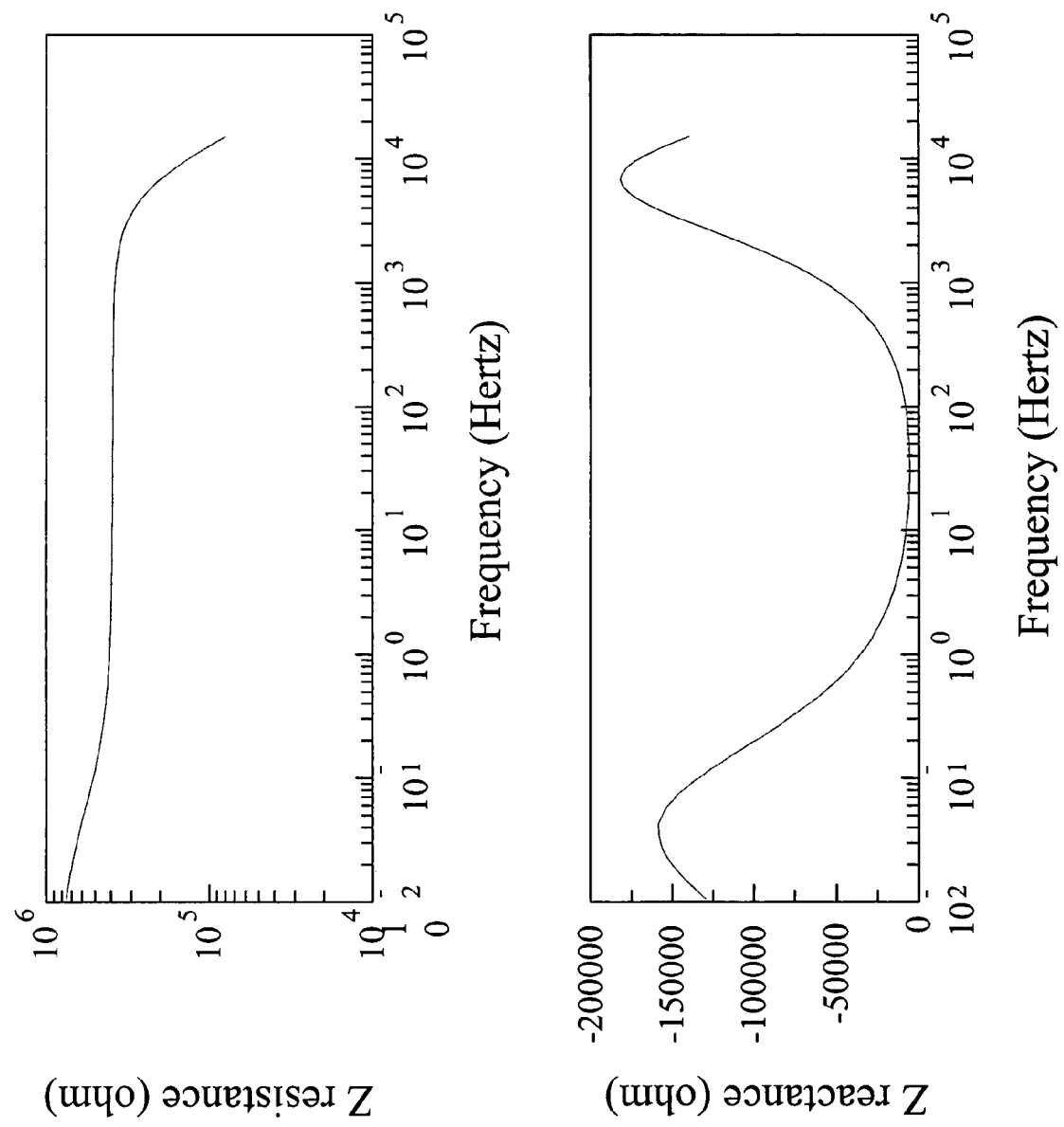
FIG. 2 is an illustration of typical impedance spectroscopy data shown as a Bode plot.

Referring now to FIG. 2, typical IS data are illustrated in the form of Bode plots, which are well-known to persons skilled in the electronic arts. The upper plot shows the resistive part of impedance versus the logarithm of frequency. The lower plot shows the reactive part of impedance versus the logarithm of frequency. These exemplary data represent an IS spectrum for a lubricant fluid.

Although the data are shown as continuous curves in FIG. 2, persons skilled in the arts of scientific data acquisition will understand that the curves actually represent a plurality of connected point measurements. For example, the curves may comprise ten data points per decade. Alternatively, far fewer points may be employed, as are used in U.S. Pat. No. 6,278,281 cited above, wherein only two points are used to practice the invention described therein. In some exemplary embodiments of the present invention, IS spectra data includes at least three points, and typically includes tens or hundreds of points. More than a few hundred points are not usually required. For the practice of the present invention, the IS spectra points will generally (although exceptions may occur) span a frequency range sufficient to represent IS characteristics associated with both the bulk fluid properties and with the interface between the fluid and the electrode (the fluid/electrode interface). These IS characteristics and their frequency ranges are described in more detail hereinbelow. In general, the IS spectra employed will include frequencies both above and below 1 Hz.

Figure 3:
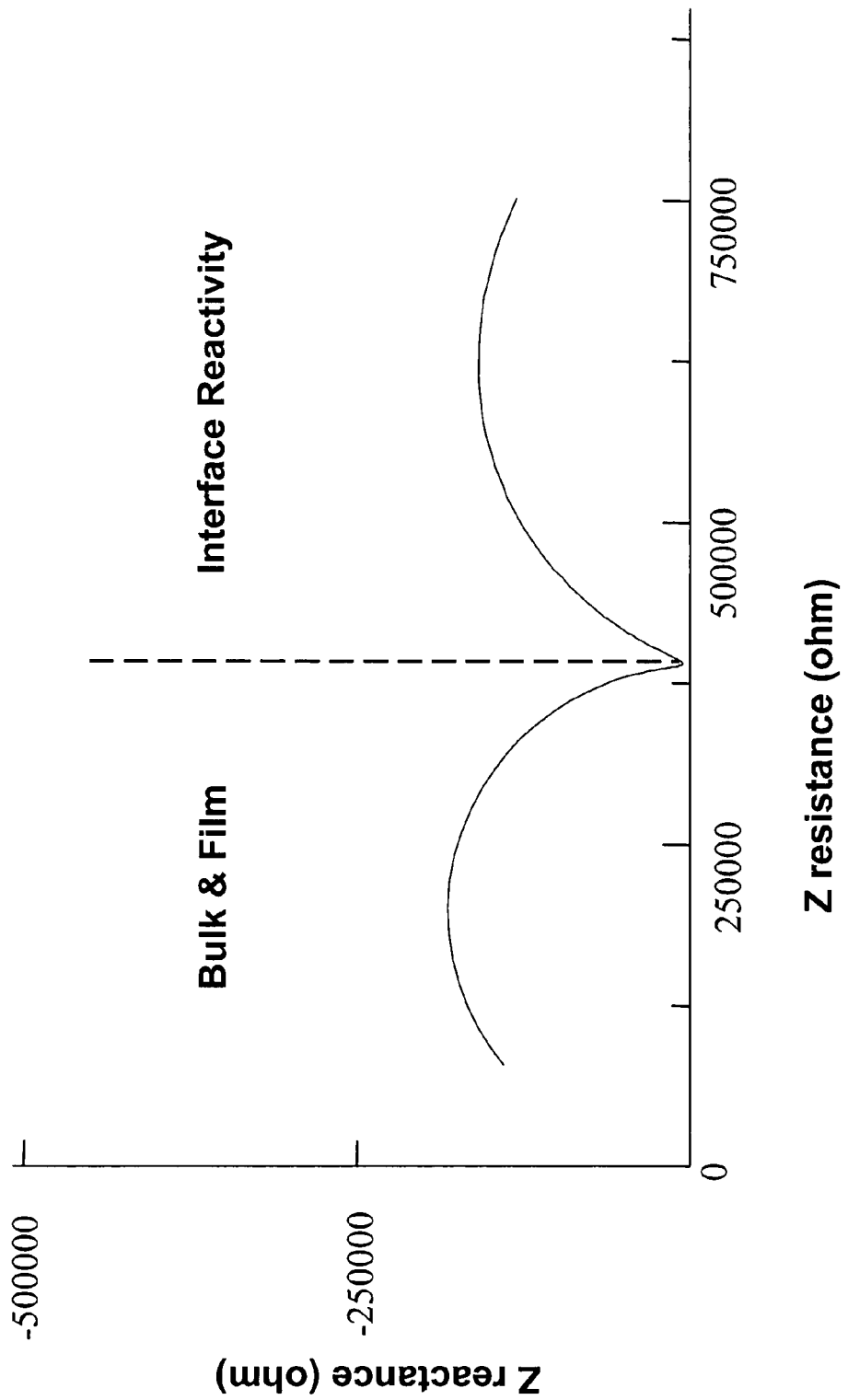
FIG. 3 is an illustration of typical impedance spectroscopy data shown as a Nyquist plot.

FIG. 3 illustrates the same IS data depicted in FIG. 2, using a Nyquist plot, which is well known to persons skilled in the electronic arts. The data show a minimum in the reactance, known as the "Nyquist minimum". As described below in more detail, data for frequencies lower than the Nyquist minimum can be associated with an interface reactivity caused by electrically-active phenomena occurring at the fluid/electrode interface. Data for frequencies greater than the minimum can be associated with the electrical properties of the fluid bulk, and with a fluid film present on the electrode.

Exemplary Data Analysis Using Equivalent Circuit Modeling

Figure 4:
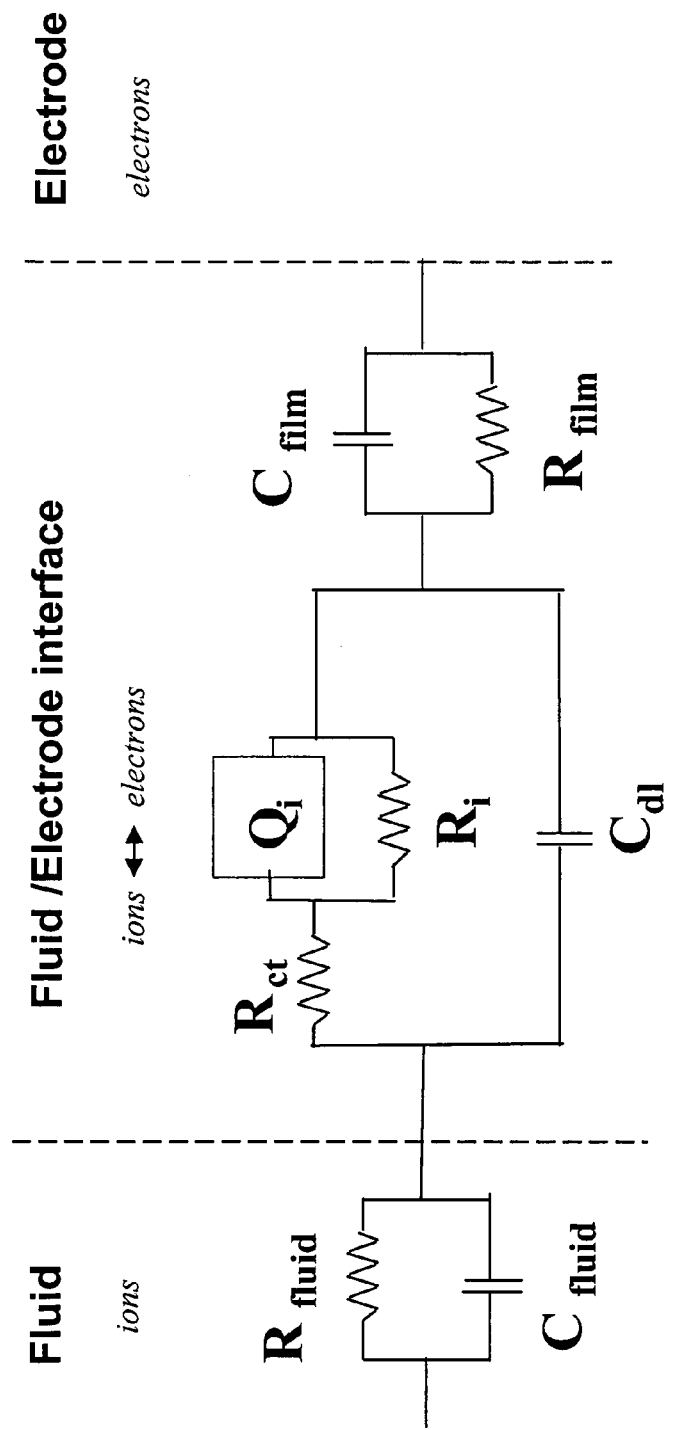
FIG. 4 is an illustration of an equivalent circuit for modeling impedance spectra data.

FIG. 4 shows an equivalent circuit model that may be used to assist data analysis in accordance with one embodiment of the present invention.

As shown in FIG. 4, there is an impedance associated with the bulk fluid electrical properties comprising $R_{fluid}$ and $C_{fluid}$, having a time constant $\tau_{fluid}$ as follows:

$$\tau_{fluid} = R_{fluid} C_{fluid}$$

Persons skilled in the electrochemical arts shall recognize that for many fluids, such as lubricating fluids, the bulk electrical transport occurs primarily via ionic conduction. For fluids exhibiting ionic conduction, there is also impedance associated with the fluid/electrode interface. The electrical phenomena resulting from contact between the fluid and the electrode surface is represented in FIG. 4 by elements shown between the vertical dashed lines. The interfacial impedance includes a capacitance $C_{d1}$ created by polarization arising from a double layer formation, as ions orient themselves in response to the presence of the charged metal surface. Because the fluid is an ionic conductor, and the electrode an electronic conductor, a charge transfer reaction must be operative for current to flow across the interface fluid/electrode. This current leakage across the fluid/electrode interface is represented in FIG. 4 by a parallel path.

As shown in FIG. 4, charge transport is accompanied by energy that is required for charge transfer, represented by a resistance $R_{ct}$, and possibly adsorption, and/or diffusion as detectable steps in the overall process. The specific nature of this electro-chemical reaction determines the form of the detected impedance associated with this reaction path. If the reaction is fast, a diffusion-limited character is often evident. Conversely, reactions involving slow kinetics, i.e. reactions involving rate-limiting adsorption of intermediate species, yield impedance character of a different form. When sufficiently defined from measured data, an interface time constant value $\tau_i$ can be defined in a manner that is analogous to the bulk value. The interface time constant $\tau_i$ reflects either the heterogeneous rate constant of the reaction or the magnitude of the diffusion coefficient for the reacting species (reactant or product). This provides an effective value for the net reactivity of species at the fluid/electrode interface, and is calculated from the following relationship:

$$\tau_i = (R_i Q_i)^{1/n},$$

where observed values of n range between 0.5–1.0. The observation of diffusion as rate-limiting implies that the rate of reaction at the surface is fast as the potential is modulated by an AC signal, such that local depletion (or accumulation) of the surface-active species occurs. The presence of this gradient in concentration is observed in the measured impedance as a Constant Phase Element (CPE), denoted as $Q_i$, where the CPE exponent n is equal to 0.5. The determination of n-values for interfacial phenomena at or close to unity is indicative of adsorption as the rate-limiting step at the electrode.

Referring again to FIG. 4, another interface time constant, $\tau_{film}$, may also be observed. For appropriately configured measurements and fluid samples, this value is determined according to the following equation:

$$\tau_{film} = R_{film} C_{film},$$

where the resistance $R_{film}$, and the capacitance $C_{film}$, reflect the electrical properties and geometry of the fluid film that may form on the electrode.

Impedance data analysis in accordance with the above described equivalent circuit model may be performed by the data processing system 110 of FIG. 1, using the well known Complex Non-Linear Least Squares fitting technique employed by the PC-based computer program, "Equivalent Circuit", written by Boukamp (B. A. Boukamp, "Equivalent Circuit (*Equivckt. PAS*)" User's Manual, Dept. of Chemical Technology, Universiteit Twente, Netherlands, 1988 and 1989. This fitting technique is also described in an article written by B. A. Boukamp, "A Nonlinear Least Squares Fit procedure For Analysis of Immitance Data of Electrochemical Systems" Solid State Ionics, Vol. 20, pp. 31–44, 1986). The above-cited User's Manual and article are incorporated by reference herein for their teachings on data analysis.

The results of the equivalent circuit data analysis technique described above include values for the circuit elements shown in FIG. 4. These values represent characteristics, or "IS signatures" that may be employed for monitoring fluid properties in accordance with the present invention. The equivalent circuit model and corresponding data analysis given above is by way of example only. The scope of the present invention also encompasses the use of other equivalent circuit models and associated analysis techniques that suitably represent IS measurements and properties of fluids.

Exemplary Data Analysis Using Statistical Techniques

In addition to the equivalent circuit data analysis technique described above, the data analysis processes implemented by the data processing system 110 may include one or more well known statistical techniques. For example, the data analysis performed by the data processing system 110 may include the following techniques: Principal Component Analysis (PCA), Multivariate Least Squares Regression (MLR), Principal Component Regression (PCR), Pattern Recognition analysis, Cluster analysis, and Neural Net analysis. A description of these techniques in reference to IS data analysis is disclosed in the co-pending U.S. patent application, application Ser. No. 10/723,624, filed Nov. 26, 2003, titled "FLUID CONDITION MONITORING USING BROAD SPECTRUM IMPEDANCE SPECTROSCOPY" (Eaton Ref. No. 03-ASD-255(SR)). This above-incorporated application is set forth in full in Appendix A of the present application.

Exemplary commercially available software that may be used by the data processing system 110 of FIG. 1 in implementing the processes required for the statistical analysis techniques include the following software applications: "The Unscrambler™" by Camo Process™, AS; Norway; Spectrum Quant+™ by PerkinElmer™, Inc., Norwalk, Conn.; and MatLab™ by Mathworks™, Inc., Natick, Mass.

Exemplary Data—Determination of IS Signatures for Calibration Fluids

This section describes experimental results that illustrate the application of IS measurements and analysis to lubricating oils. IS measurements are performed on an exemplary calibration set of sample fluids, the IS data are analyzed, and IS signatures are obtained indicative of fluid properties and additive concentrations.

The exemplary calibration samples were formulated from a base oil (BO) by blending into the BO two additive components: 1) a Detergent-Inhibited package (DI), and 2) a viscosity index improver (VII). Because the blending operation is typically performed at 60° C., the IS measurements were performed at this temperature.

As persons skilled in the arts of lubricant manufacture will understand, there are many variations for BO and additive types that may be employed in accordance with the present inventive concept. For the present example, the BO was a mineral oil type, mixed paraffinic/naphthenic of two different distillation ranges (i.e., molecular weights). The DI package was a typical non-ZDDP (zinc dithiodialkylphosphate) application type package containing a dispersant, detergents, antioxidant and antiwear components. The VII used was an olefin copolymer. Although the detailed effects on IS data would vary for different BOs and additive types, the principles of the inventive concept as illustrated by these exemplary samples would remain the same.

Table 1 below lists the compositions of samples.

TABLE 1

Sample Compositions

| 2 | | a | b | c | 3 | | a | b | c |
|---|---|---|---|---|---|---|---|---|---|
| DI | 14.21 | 14.2104 | 14.2102 | 14.2099 | DI | 15.3900 | 15.3897 | 15.3900 | 15.3901 |
| VII | 3.59 | 3.5906 | 3.5908 | 3.5906 | VII | 3.5900 | 3.5913 | 3.5899 | 3.5910 |
| BO | 82.2 | 82.02 | 82.2 | 82.19 | BO | 81.02 | 81.02 | 81.02 | 81.02 |
| DI low, VII high | | | | | DI high, VII high | | | | |

| | 1 | a | b | c |
|---|---|---|---|---|
| DI | 14.8 | 14.8025 | 14.8009 | 14.8018 |
| VII | 3.34 | 3.3403 | 3.3405 | 3.3405 |
| BO | 81.86 | 81.87 | 81.87 | 81.86 |
| DI spec, VII spec | | | | |

| 4 | | a | b | c | 5 | | a | b | c |
|---|---|---|---|---|---|---|---|---|---|
| DI | 14.21 | 14.2097 | 14.2101 | 14.2102 | DI | 15.39 | 15.3904 | 15.3899 | 15.3907 |
| VII | 3.09 | 3.0908 | 3.0895 | 3.0902 | VII | 3.09 | 3.0908 | 3.0916 | 3.0897 |
| BO | 82.7 | 82.70 | 82.69 | 82.71 | BO | 81.52 | 81.52 | 81.53 | 81.52 |
| DI low, VII low | | | | | DI high, VII low | | | | |

The table entries not shown in bold in Table 1 represent the component concentrations in percent. The central samples 1 are lubricant blends with desired (spec) values of additive concentrations. The samples 2 and 4 have DI concentrations that are 4% below spec and the samples 3 and 5 have DI concentrations that are 4% above spec. The samples 2 and 3 have VII concentrations that are 4% above spec, and the samples 4 and 5 have VII concentrations that are 4% below spec. Blend samples a and b were prepared from the same batch of DI-additive. Blend samples c were prepared from a different batch of DI-additive. All blend samples were made from the same batch of VII and base oil.

Figure 5:
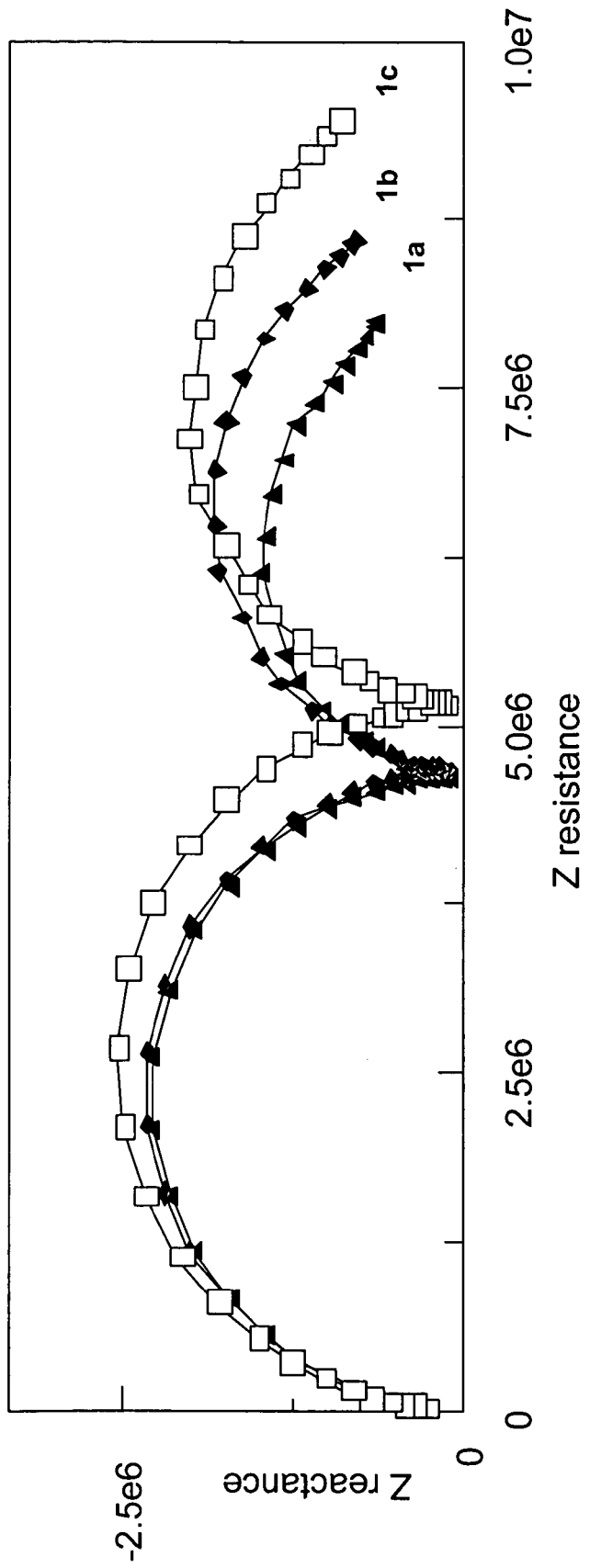
FIG. 5 is a plot of typical impedance spectroscopy data obtained for selected exemplary calibration fluids.

FIG. 5 shows typical data for samples 1a, 1b and 1c presented as a Bode plot. The frequency range is from 7.5 kHz to 7.5 mHz for data points from left to right, with 10 data points per decade.

The measured impedance data for each sample was then evaluated using PCA to recast the measured impedance in terms of a new set of independent variables (principal components or "PCs"), each containing weighted contributions from all of the AC frequencies acquired. Principal Component Analysis (PCA) is a technique well known to those skilled in the art of data analysis. Those PCs responsible for the largest variance present within the data set were then regressed against the property value(s) of interest (Principal Component Regression, or "PCR"). This method was employed individually for the real (resistance) and imaginary (reactance) components of the measured impedances. From these analyses, meaningful regressions were obtained for the real component of impedance, against both Ca and $CO_3$ ion concentrations, but not against viscosity.

Figure 6:
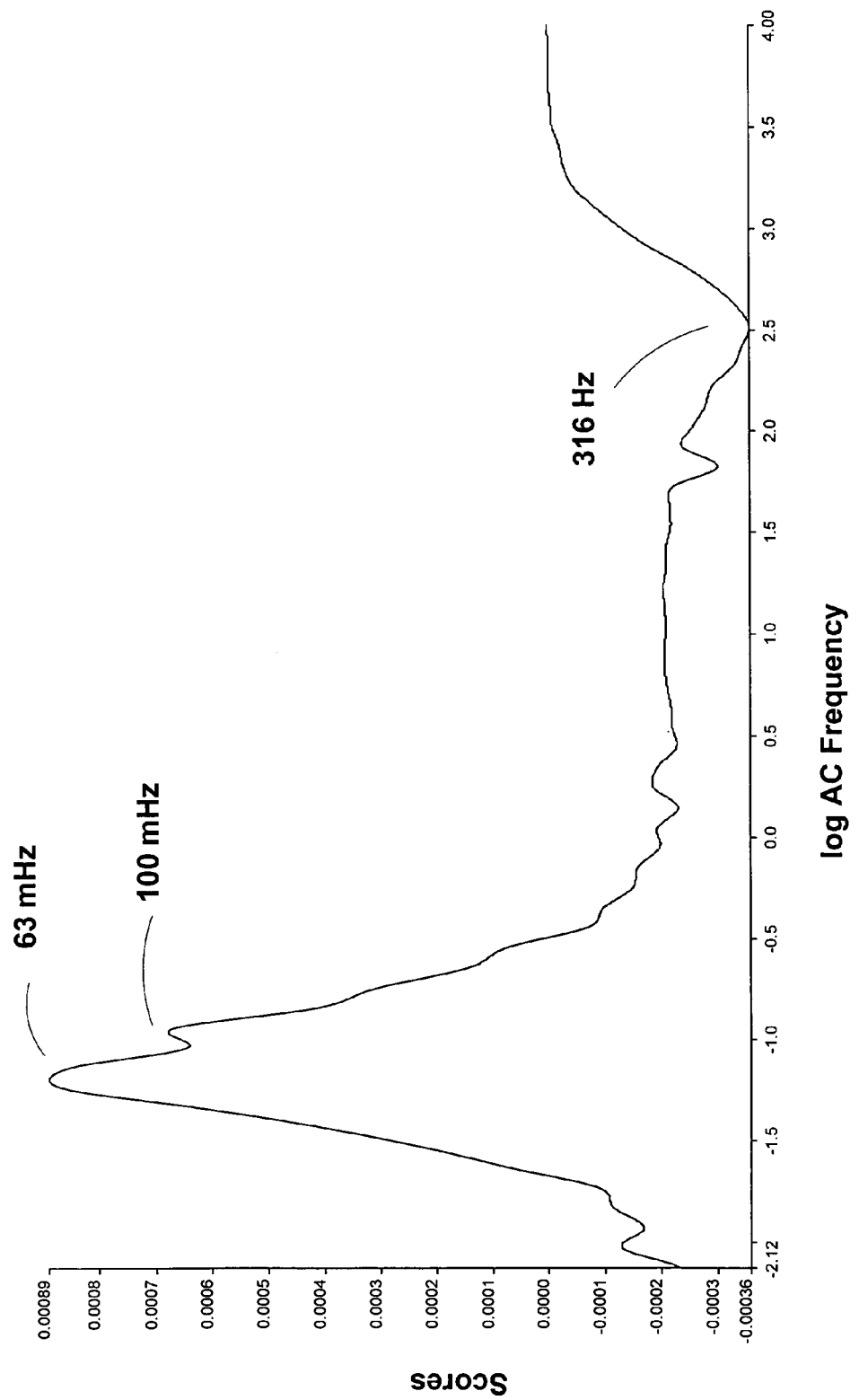
FIG. 6 is a plot of a Regression Summary for impedance spectroscopy data relating to Ca concentration for exemplary calibration fluids.

FIG. 6 illustrates the summary of the regression of the two major PCs determined from the AC resistance values against the measured Ca values. Referring to FIG. 6, it can be observed that peaks occur at 316 Hz, 100 mHz, and 63 mHz, indicating that the measured values at these frequencies are strongly influenced by Ca concentration. These PCs, peaks, and the corresponding sets of data points, exemplify some of the characteristics, or IS signatures, that may be obtained using statistical analysis techniques on the IS data.

As a result, the raw data at these frequencies (both resistance and reactance) can be provided as input into a second technique known as "Group Method For Data Handling (GMDH)." GMDH is a method that is generally known to persons of ordinary skill in the art of data analysis. The GMDH method facilitates development of non-linear correlation to property(s) of interest. The resulting model for Ca concentration is shown in FIG. 7.

Figure 8:
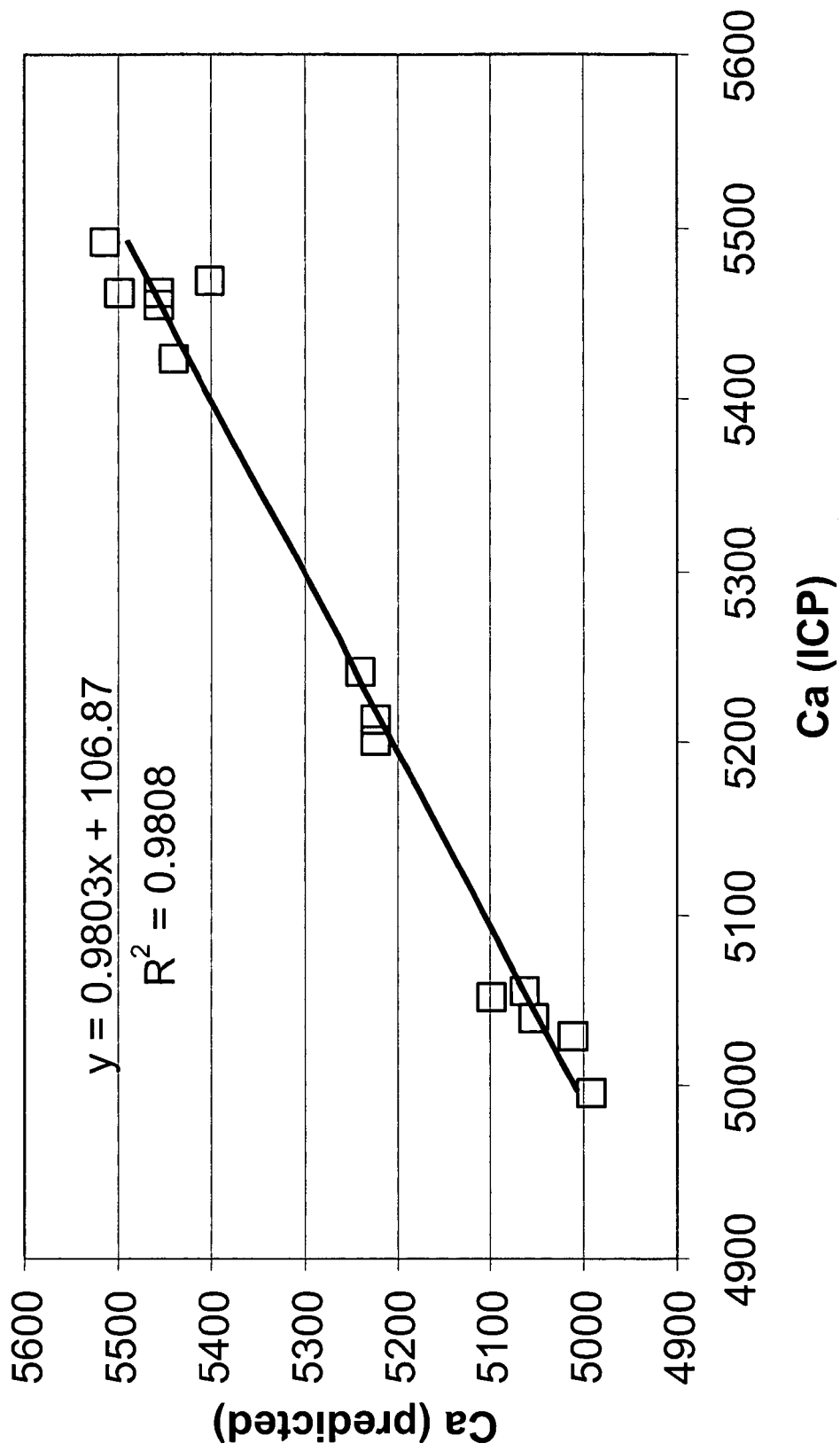
FIG. 8 is a plot of Ca concentration from analytical measures versus impedance spectroscopy model predicted values for exemplary calibration fluids.

As is seen in FIG. 8, the GMDH analysis of FIG. 7 yields predicted ("predicted" indicates the value that would be inferred from IS measurements) Ca values that are well-correlated to those determined from the traditional analytical measurement method (ICP).

Figure 9:
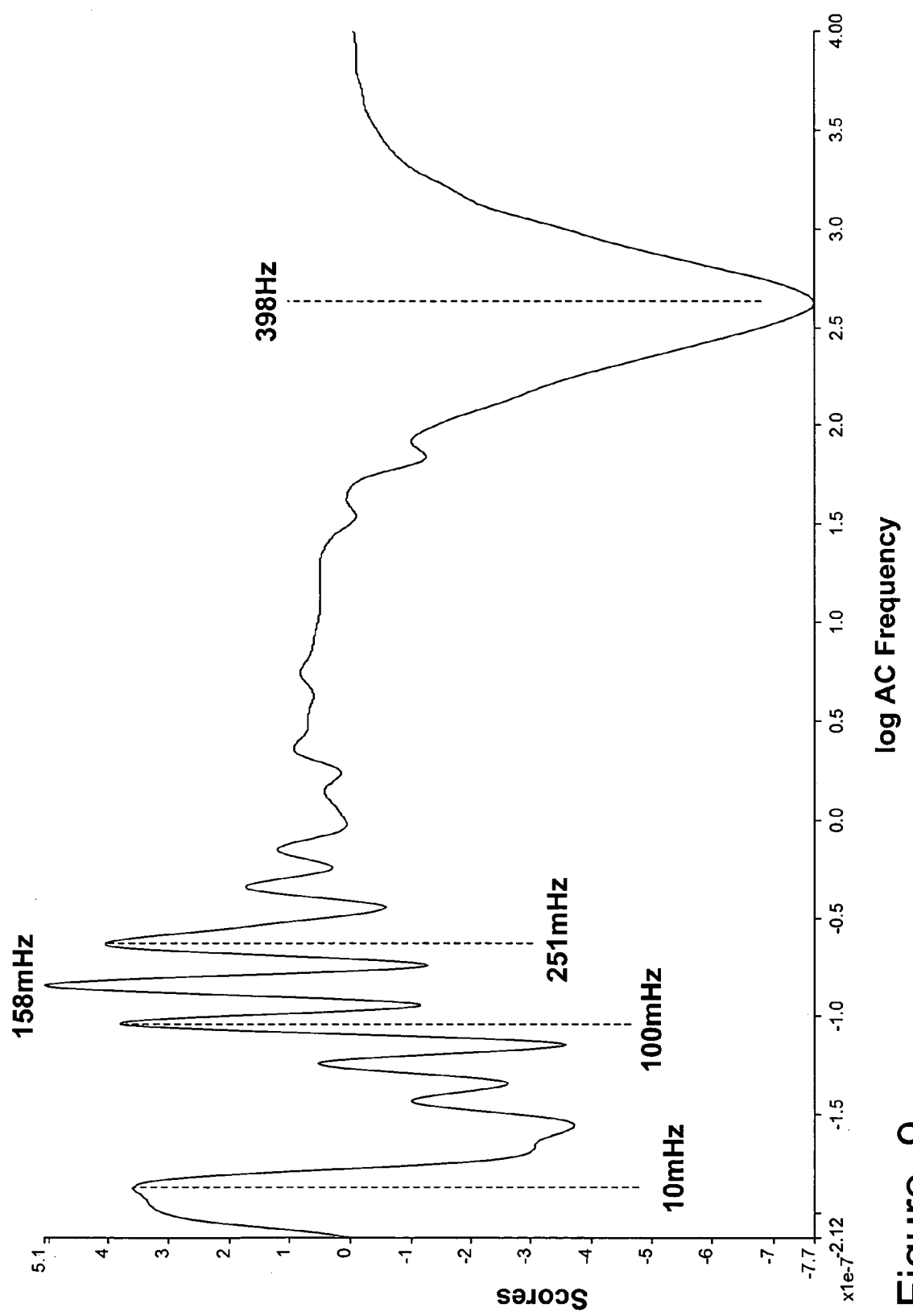
FIG. 9 is a plot of a Regression Summary for impedance spectroscopy data relating to $CO_3$ concentration for exemplary calibration fluids.

The procedures described above may also be applied using $CO_3$ concentrations determined from analysis of Fourier Transform Infrared (FTIR) spectra. In this case, a more complicated regression output can be observed, as illustrated in FIG. 9. As noted above, these PCs, peaks, and the corresponding sets of data points, exemplify some of the characteristics, or IS signatures, that may be obtained from using statistical analysis techniques on the IS data.

Figure 11:
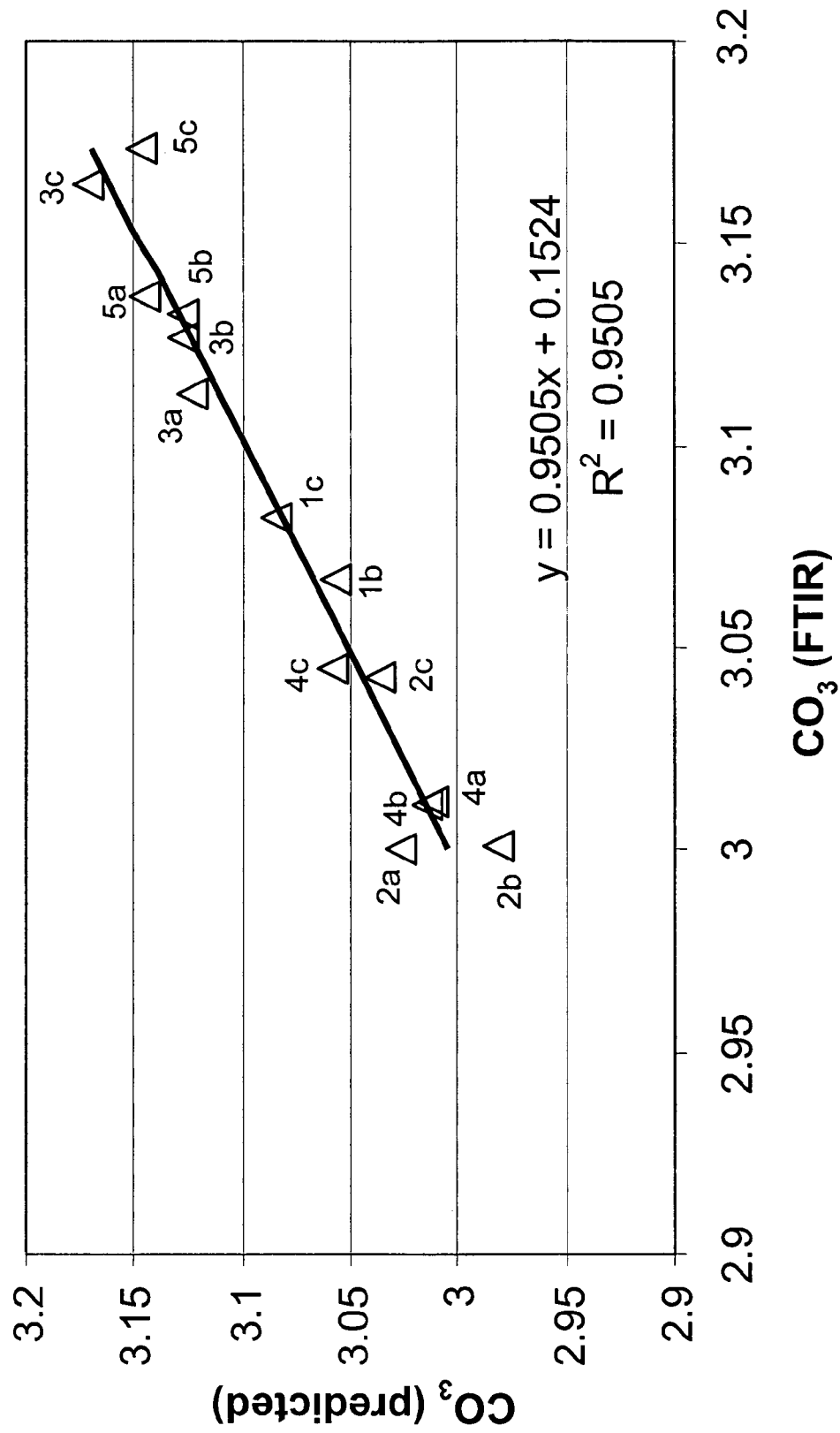
FIG. 11 is a plot of $CO_3$ concentration from analytical measures versus impedance spectroscopy model predicted values for exemplary calibration fluids.

Analogous to the Ca determination, the raw impedance data at the five frequencies corresponding to the major peaks in this summary may be utilized to establish a correlation. This involves using Multiple Linear Regression (MLR), where the coefficients determined for each input value are shown in FIG. 10. As seen in FIG. 11, a high degree of correlation between the predicted and measured values may be obtained.

These exemplary data may also be analyzed using equivalent circuit modeling as described above. The analysis of the data provides three time constants in accordance with a model as shown in FIG. 4.

Figure 12:
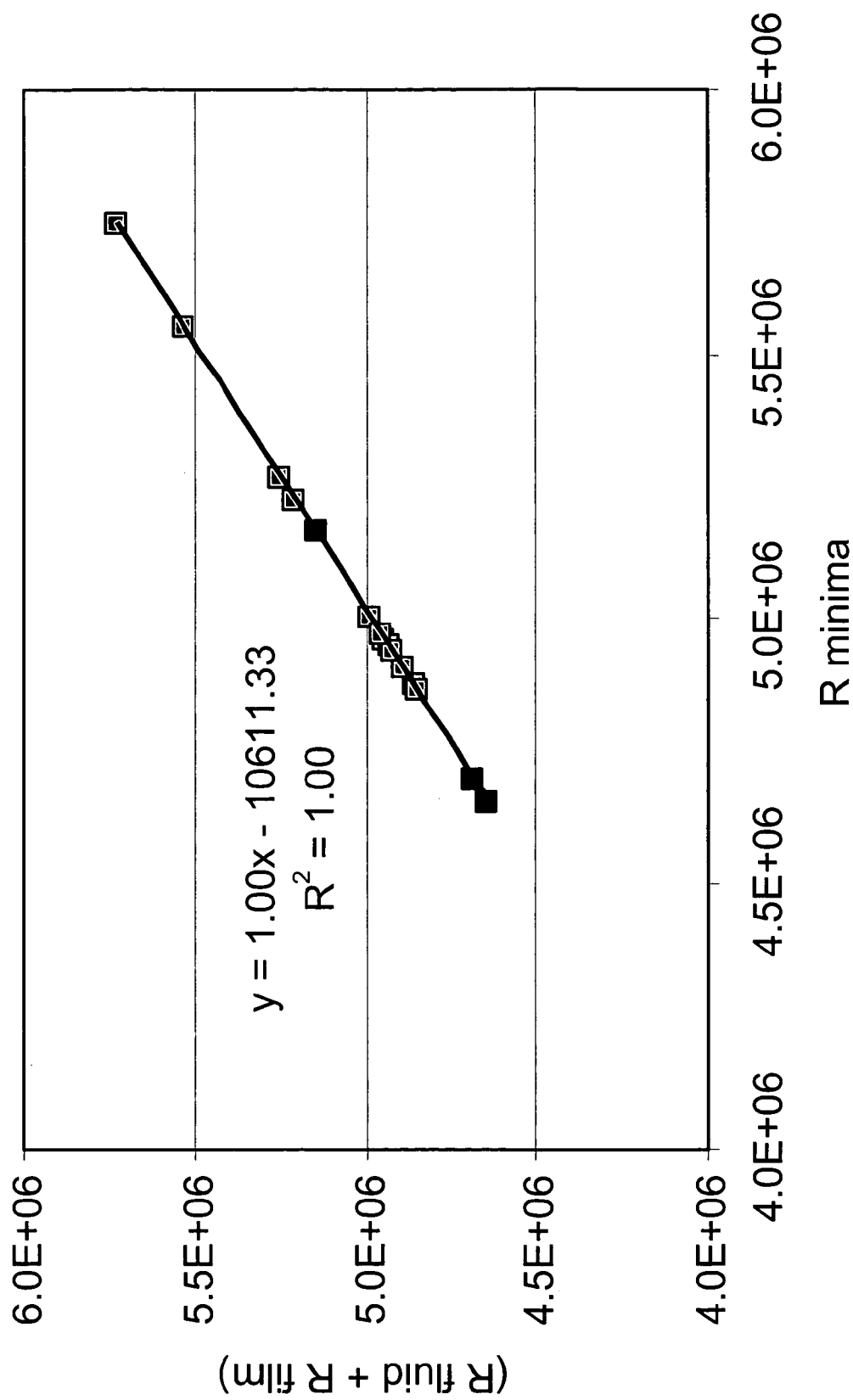
FIG. 12 is a plot of equivalent circuit parameters ($R_{fluid}$+$R_{film}$) versus $R_{minima}$ for exemplary calibration fluids.

The data analysis also provides values for the equivalent circuit parameters $R_{fluid}$, $R_{film}$, and $R_{minima}$, where $R_{minima}$ is the resistance observed at the Nyquist minima. FIG. 12 shows the relationship between the sums of the $R_{fluid}$ and $R_{film}$ and the $R_{minima}$. The time constraints and equivalent circuits parameters exemplify some of the characteristics or IS signatures that may be obtained from the IS data by equivalent circuit modeling analysis techniques.

FIG. 12 demonstrates that the sum of the modeled resistance values ($R_{fluid}$+$R_{film}$) underlying the measured high frequency response is equal to $R_{minima}$. This agreement is useful in that the measured resistance value can be divided by the corresponding measured viscosity (VIS) value for all blend samples. This ratio can thus be compared to the IS predicted $Ca/CO_3$ ratio, in accordance with the following equation:

$$R_{minima}/VIS = y0 + A1 \exp^{(-(x-x0)/t1)}$$

Figure 13:
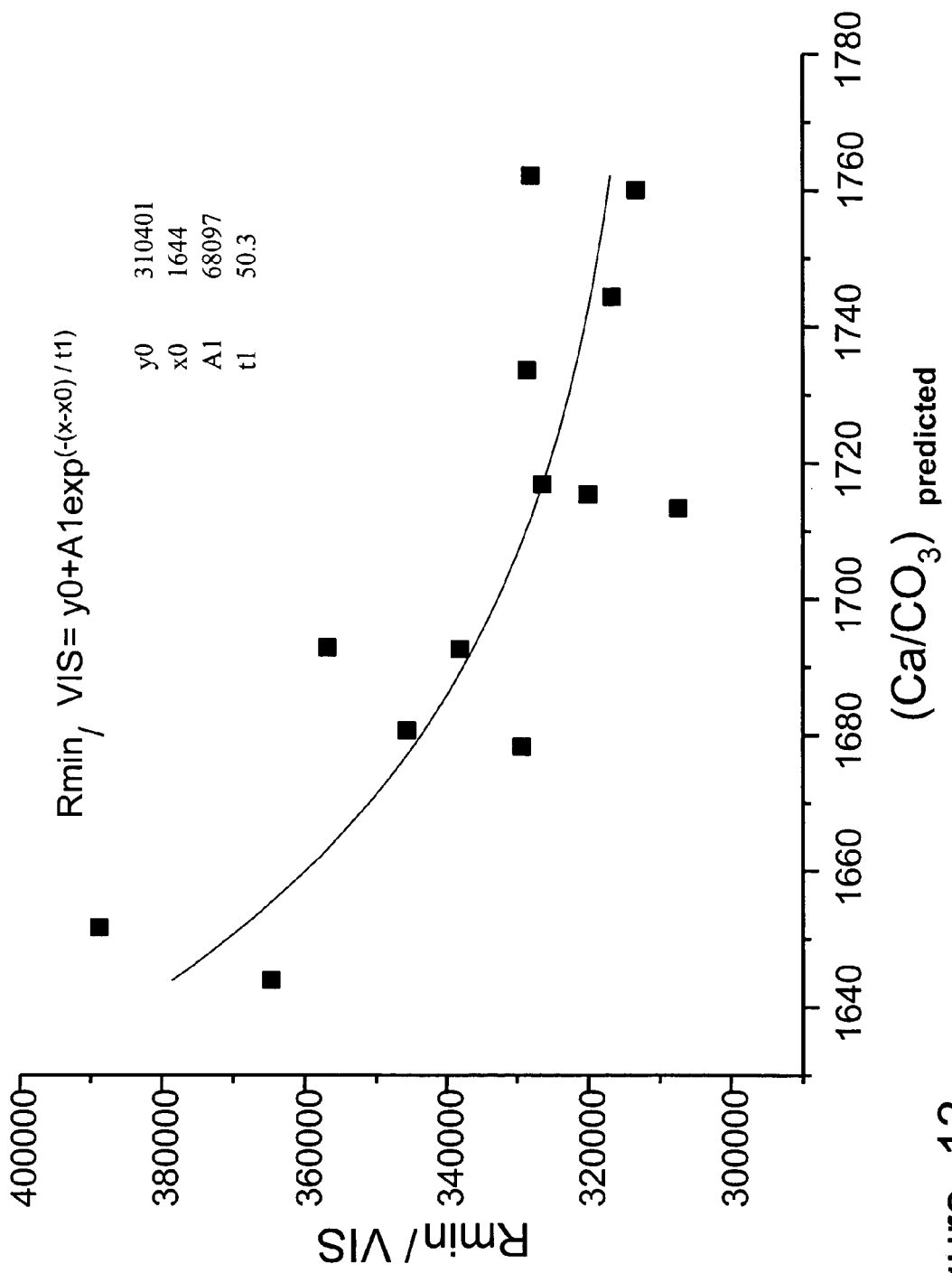
FIG. 13 is a plot of $R_{minima}$/viscosity versus predicted Ca/$CO_3$ ratio for exemplary calibration fluids.

Referring to the data illustrated in FIG. 13, the best-fit values for the parameters in the equation above are as follows: y0=310401, x0=1644, A1=68097, and t1=503. In accordance with the present example, this comparison method enables a viscosity estimation to be made using IS data that is accurate to within plus or minus 1 centiStoke to the traditional analytical measurement method (kinematic viscosity). Persons with skill in the electrochemical arts will understand that this an exemplary result only, and application of the method to other data will, in general, yield other equation parameters and accuracy of results.

Although the practice of the present inventive concept is not limited to lubricating fluids, many advantageous embodiments may include lubricating fluid formulations. A lubricating fluid formulation may consist of a BO incorporating one or more additives. Exemplary BO types may include, without limitation, the following categories: mineral base and synthetic base. Exemplary additive types may include, without limitation, the following categories: viscosity modifiers, pour point depressants, stabilizers, seal swell agents, anti-static additives, antioxidants, metal deactivators, anti-foam agents, detergents, dispersants, anti-wear additives, and corrosion inhibitors.

Other exemplary fluids that may be used with embodiments of the present inventive concept may include, without limitation, fuel treatment additives and top treatments. A fuel treatment fluid may include an additive and a dilutant (such as kerosene or other fuel), wherein a typical additive may include a DI, VII, etc. A top treatment may include an additive (such a DI, VII, etc.) and a dilutant or BO.

Exemplary Method of Operation

Figure 14:
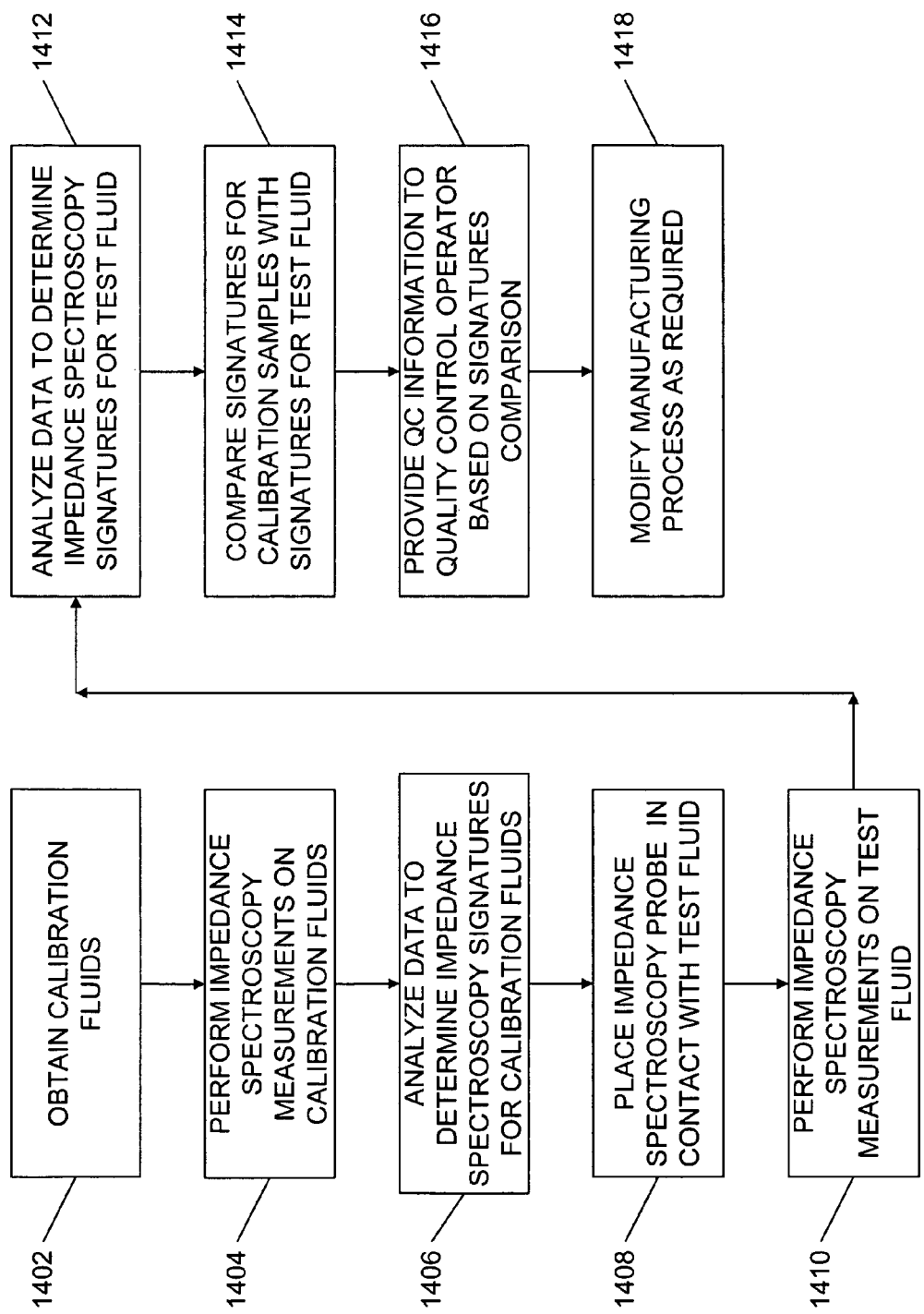
FIG. 14 is a flowchart diagram of an exemplary method using Impedance Spectroscopy to monitor and control fluid properties according to the present inventive concept.

In accordance with the present invention, an exemplary method of using IS to monitor and control fluid properties may include the following STEPS 1402 to 1418 as illustrated by the flowchart diagram of FIG. 14.

At a STEP 1402, a calibration set of samples or fluids having known properties, such as known additive concentrations, is obtained. In one aspect of the inventive concept, the calibration set of samples may be chosen to be representative of a manufacturing process (e.g., a blending operation). For example, a suitable set of calibration samples may include variations in concentrations of additives to a base fluid reflective of specified values and limits for the additive concentrations. The practice of the inventive concept also includes using a single calibration fluid, and specifying acceptable variations (e.g., plus or minus 10 percent) for the IS signatures as defined below. The method then proceeds to a STEP 1404.

At the STEP 1404, IS measurements are performed on the calibration samples to provide calibration data for analysis. The method next proceeds to a STEP 1406.

At the STEP 1406, the IS data are analyzed using statistical techniques, equivalent circuit modeling techniques, or a combination thereof. The data analysis provides IS signatures indicative of the properties of the calibration samples. For example, the IS signatures may be correlated with variations in Ca concentration, $CO_3$ concentration, and viscosity. Persons skilled in the lubricant engineering arts will recognize that these properties can be related to additive concentrations such as DI and VII. The IS signature calibration data may be stored by a data processor such as the data processing system 110 of FIG. 1. The method next proceeds to a STEP 1408.

At the STEP 1408, an IS probe is placed in contact with a test sample or test fluid for the purpose monitoring the properties of the test fluid. The test fluid may, for example, be related to a manufacturing process such as a blending operation. As illustrated in FIG. 1, the IS probe 106 may be placed in contact with the fluid 104 contained within the container 102. In this example, as previously noted, the container may be a blending tank or in-line blending container, and the fluid 104 may be a lubricant, or a lubricant additive package, which is undergoing a blending operation. The lubricant or lubricant additive package may have additives or components corresponding to the calibration samples. The method next proceeds to a STEP 1410.

At the STEP 1410, an impedance spectrometer, such as the spectrometer 106 of FIG. 1, is used to make IS measurements on the test fluid via the IS probe. As previously noted, in one exemplary embodiment, for the practice of the present invention, the IS data will include at least three points, and typically will include tens or hundreds of points. More than a few hundred points are not usually required. Also, as described above, in some embodiments, the IS data points will generally (exceptions may occur) span a frequency range sufficient to represent IS characteristics associated with both the bulk fluid properties and with fluid/electrode interface. In general, the IS spectra employed will include frequencies both above and below 1 Hz. The method next proceeds to a STEP 1412.

At the STEP 1412, the measurements from the impedance spectrometer are provided to a data processing system, or data processor, such as a personal computer. The data are analyzed using statistical techniques, equivalent circuit modeling techniques, or a combination thereof, to determine IS signatures indicative of the properties of the test fluid. The method next proceeds to a STEP 1414.

At the STEP 1414, the IS signatures for the test fluid obtained from the data analysis are compared quantitatively with the IS signatures of the calibration samples. For example, a comparison of the IS signature indicative of Ca concentration may show that the Ca concentration for the test fluid exceeds the maximum Ca concentration for the calibration sample set. As noted above, in another aspect of the inventive method, a single calibration fluid may be used, and acceptable variations (e.g., plus or minus 10 percent) for the IS signatures of the test fluid relative to the IS signatures of the calibration fluid may be specified. The method next proceeds to a STEP 1416.

At the STEP 1416, the data processor provides quality control information to a quality control operator relating to the results of STEP 1414. For example, if the test fluid is found to be outside a specified range for an additive concentration, the operator may be notified accordingly. Test results may also be recorded by the data processing system for future reference. The method next proceeds to a STEP 1418.

At the STEP 1418, based on the quality control information received from the data processing system, the quality control operator may modify the manufacturing process, as required. In one embodiment, the test fluid may be modified in order to maintain or correct the properties of the test fluid with respect to specified limits. For example, the modifications or adjustments may be directed to changing the concentrations of additives in a lubricant during a blending process, or to changing the relative concentrations of components in a lubricant additive package.

Figure 15:
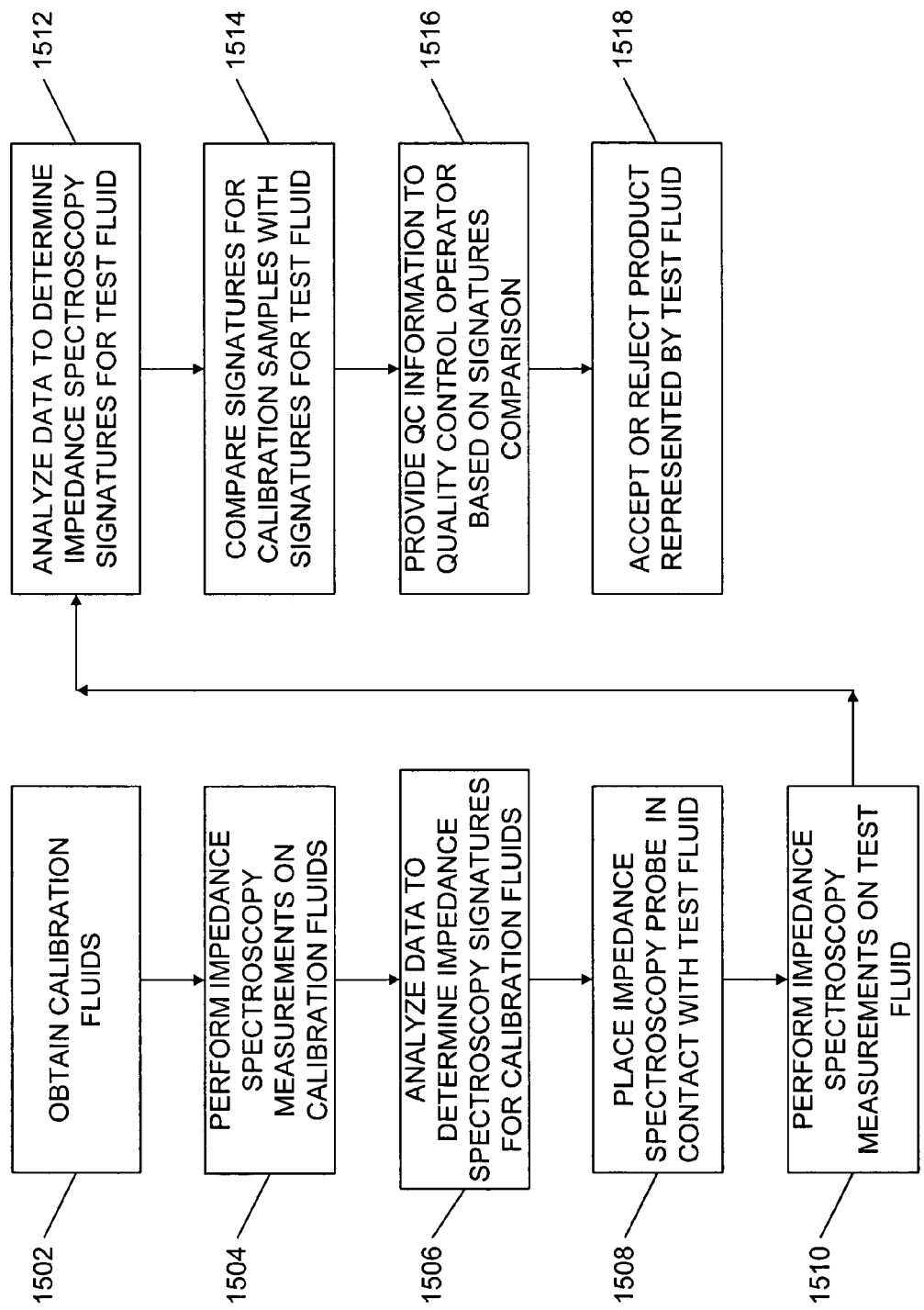
FIG. 15 is a flowchart diagram of another exemplary method using Impedance Spectroscopy to monitor and control fluid properties, illustrating another embodiment of the inventive concept.

FIG. 15 is a flowchart diagram illustrating another embodiment of the inventive concept.

At a STEP 1502, a calibration set of samples or fluids having known properties, such as known additive concentrations, is obtained. In this exemplary embodiment, the calibration set of samples may be representative of a genuine product that is to be compared with a test fluid of unknown authenticity. In another aspect, the calibration set of samples may be representative of a product having acceptable properties that is to be compared with a test fluid of unknown properties or quality. For example, a suitable set of calibration samples may include variations in concentrations of additives to a base fluid reflective of specified values and limits for the additive concentrations. The practice of the inventive concept also includes using a single calibration fluid, and specifying acceptable variations (e.g., plus or minus 10 percent) for the IS signatures as defined below. The method then proceeds to a STEP 1504.

At the STEP 1504, IS measurements are performed on the calibration samples to provide calibration data for analysis. The method next proceeds to a STEP 1506.

At the STEP 1506, the IS data are analyzed using statistical techniques, equivalent circuit modeling techniques, or a combination thereof. The data analysis provides IS signatures indicative of the properties of the calibration samples. For example, the IS signatures may be correlated with variations in Ca concentration, $CO_3$ concentration, and viscosity. Persons skilled in the lubricant engineering arts will recognize that these properties can be related to additive concentrations such as DI and VII. The IS signature calibration data may be stored by a data processor such as the data processing system 110 of FIG. 1. The method next proceeds to a STEP 1508.

At the STEP 1508, an IS probe is placed in contact with a test sample or test fluid for the purpose monitoring the properties of the test fluid. The test fluid may be a sample representative of a product to be tested for authenticity. In this aspect, the inventive method detects counterfeit products, such as lubricants, that may have been substituted for a genuine product. Alternatively, the test fluid may be sample representative of a product of unknown quality. In this aspect, the inventive method detects products having properties not in conformance with acceptable quality. As illustrated in FIG. 1, the IS probe 106 may be placed in contact with the fluid 104 contained within the container 102. The test fluid may have additives or components corresponding to the calibration samples. The method next proceeds to a STEP 1510.

At the STEP 1510, an impedance spectrometer, such as the spectrometer 106 of FIG. 1, is used to make IS measurements on the test fluid via the IS probe. As previously noted, in one exemplary embodiment, for the practice of the present invention, the IS data will include at least three points, and typically will include tens or hundreds of points. More than a few hundred points are not usually required. Also, as described above, in some embodiments, the IS data points will generally (exceptions may occur) span a frequency range sufficient to represent IS characteristics associated with both the bulk fluid properties and with fluid/electrode interface. In general, the IS spectra employed will include frequencies both above and below 1 Hz. The method next proceeds to a STEP 1512.

At the STEP 1512, the measurements from the impedance spectrometer are provided to a data processing system, or data processor, such as a personal computer. The data are analyzed using statistical techniques, equivalent circuit modeling techniques, or a combination thereof, to determine IS signatures indicative of the properties of the test fluid. The method next proceeds to a STEP 1514.

At the STEP 1514, the IS signatures for the test fluid obtained from the data analysis are compared quantitatively with the IS signatures of the calibration samples. For example, a comparison of the IS signature indicative of Ca concentration may show that the Ca concentration for the test fluid exceeds the maximum Ca concentration for the calibration sample set. As noted above, in another aspect of the inventive method, a single calibration fluid may be used, and acceptable variations (e.g., plus or minus 10 percent) for the IS signatures of the test fluid relative to the IS signatures of the calibration fluid may be specified. The method next proceeds to a STEP 1516.

At the STEP 1516, the data processor provides quality control information to a quality control operator relating to the results of STEP 1514. For example, if the test fluid is found to be outside a specified range for an additive concentration, the operator may be notified accordingly. Test results may also be recorded by the data processing system for future reference. The method next proceeds to a STEP 1518.

At the STEP 1518, based on the quality control information received from the data processing system, the quality control operator may accept or reject the product of which the test fluid is representative, as required. For example, the quality control information may indicate that the test fluid is a sample representative of a counterfeit product. In this case, the quality control operator may take appropriate action to reject the counterfeit product. Alternatively, the quality control information may indicate that the test fluid is a sample of a product that is of unsatisfactory quality. In this case, the quality control operator takes appropriate action to reject the product.

The above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the field of determining fluid conditions and IS signatures using impedance spectroscopy and that the disclosed systems and methods will be incorporated into such future embodiments. Accordingly, it will be understood that the invention is capable of modification and variation and is limited only by the following claims.

What is claimed is:

1. A fluid property quality control method, comprising the steps of:
   a) obtaining a set of calibration fluids representative of a manufacturing process;
   b) performing impedance measurements on each of the calibration fluids to obtain first impedance spectroscopy (IS) data, wherein the first IS data include data for at least three frequencies;
   c) analyzing the first IS data providing first IS signatures indicative of properties for each of the calibration fluids;
   d) performing impedance measurements on a test fluid providing second IS data, wherein the second IS data include data for at least three frequencies;
   e) analyzing the second IS data providing second IS signatures indicative of properties of the test fluid;
   f) comparing the first IS signatures and the second IS signatures providing quality control information relating to the properties of the test fluid; and
   g) modifying the manufacturing process responsive to the quality control information;
   wherein the step of analyzing the first IS data and the step of analyzing the second IS data include equivalent circuit modeling, and the first IS signatures and the second IS signatures include at least one of the following: a bulk fluid resistance $R_{fluid}$, a bulk fluid capacitance $C_{fluid}$, a bulk fluid time constant $\tau_{fluid}$, an interface capacitance $C_{dl}$, a charge transfer resistance $R_{ct}$, an interface time constant $\tau_i$, an interface resistance $R_i$, a Constant Phase Element $Q_i$, a Constant Phase Element exponent n, a film time constant $\tau_{film}$, a film resistance $R_{film}$, and a film capacitance $C_{film}$.

2. The fluid property quality control method of claim 1, wherein the set of calibration fluids include calibration fluids having selected concentrations of at least one additive in a base fluid, and wherein the selected concentrations are representative of desired concentration limits for the at least one additive.

3. The fluid property quality control method of claim 2, wherein the base fluid includes at least one component from the following categories: mineral base oil and synthetic base oil.

4. The fluid property quality control method of claim 3, wherein the at least one additive includes at least one component selected from the following categories: viscosity modifiers, pour point depressants, stabilizers, seal swell agents, anti-static additives, antioxidants, metal deactivators, anti-foam agents, detergents, dispersants, anti-wear additives, and corrosion inhibitors.

5. The fluid property quality control method of claim 1, wherein the step of analyzing the first IS data and the step of analyzing the second IS data include statistical techniques.

6. The fluid property quality control method of claim 5, wherein the statistical techniques include at least one of the following: Principal Component Analysis, Multivariate Least Squares Regression, Principal Component Regression, Pattern Recognition analysis, Cluster analysis, Neural Net analysis, and Group Methods of Data Handling.

7. The fluid property quality control method of claim 6, wherein the first IS signatures and the second IS signatures include principal components.

8. The fluid property quality control method of claim 1, wherein the frequencies of step a) and step d) each include at least one frequency less than one Hertz, and at least one frequency greater than one Hertz.

9. The fluid property quality control method of claim 1, wherein the test fluid is a lubricant.

10. The fluid property quality control method of claim 9, wherein the step of modifying the properties of the test fluid includes modifying the concentrations of additives to the lubricant.

11. The fluid property quality control method of claim 1, wherein the test fluid is a lubricant additive package.

12. The fluid property quality control method of claim 11, wherein the step of modifying the properties of the test fluid includes modifying the concentrations of components in the lubricant additive package.

13. A quality control system controlling properties of a fluid, comprising:
   a) an impedance spectroscopy (IS) probe operatively disposed in contact with the fluid;
   b) an impedance spectrometer, operatively connected to the IS probe, wherein the impedance spectrometer performs impedance measurements on the fluid, and wherein the impedance spectrometer provides IS data for at least three distinct frequencies;
   c) a data processing system, operatively connected to the impedance spectrometer receiving the IS data, wherein the data processing system provides first IS signatures indicative of the fluid properties, and wherein the data processing system provides quality control information responsive to a comparison of the first IS signatures to a set of second IS signatures, wherein the set of second IS signatures are indicative of properties of a set of calibration fluids; and
   d) a Quality Control Operator, operatively disposed to receive the quality control information from the data processing system, and wherein the Quality Control Operator modifies the fluid properties in response to the quality control information;
   wherein the data processing system employs equivalent circuit modeling to provide the first IS signatures, and the first IS signatures and the second IS signatures include at least one of the following: a bulk fluid resistance $R_{fluid}$, a bulk fluid capacitance $C_{fluid}$, a bulk fluid time constant $\tau_{fluid}$, an interface capacitance $C_{dl}$, a charge transfer resistance $R_{ct}$, an interface time constant $\tau_i$, an interface resistance $R_i$, a Constant Phase Element $Q_i$, a Constant Phase Element exponent n, a film time constant $\tau_{film}$, a film resistance $R_{film}$, and a film capacitance $C_{film}$.

14. The quality control system of claim 13, wherein the IS probe includes concentric tubular electrodes.

15. The quality control system of claim 13, wherein the fluid is a lubricant.

16. The quality control system of claim 13, wherein the fluid is a lubricant additive package.

17. The quality control system of claim 13, wherein the data processing system includes a CPU and a memory.

18. The quality control system of claim 13, wherein the data processing system employs at least one of the following statistical techniques to provide the first IS signatures: Principal Component Analysis, Multivariate Least Squares Regression, Principal Component Regression, Pattern Recognition analysis, Cluster analysis, Neural Net analysis, and Group Methods of Data Handling.

19. The quality control system of claim 18, wherein the first IS signatures and the second IS signatures include principal components.

20. The quality control system of claim 13, wherein the set of calibration fluids include calibration fluids having selected concentrations of at least one additive in a base fluid, and wherein the selected concentrations are representative of desired concentration limits for the at least one additive.

21. The quality control system of claim 20, wherein the base fluid includes at least one component from the following categories: mineral base oil and synthetic base oil.

22. The quality control system of claim 20, wherein the at least one additive includes at least one component selected from the following categories: viscosity modifiers, pour point depressants, stabilizers, seal swell agents, anti-static additives, antioxidants, metal deactivators, anti-foam agents, detergents, dispersants, anti-wear additives, and corrosion inhibitors.

23. The quality control system of claim 13, wherein the Quality Control Operator includes at least one of the following: a person, an apparatus, and an automatic system.

24. The quality control system of claim 13, wherein the Quality Control Operator modifies the fluid properties by adjusting the concentrations of additives in the fluid.

25. The quality control system of claim 13, wherein the fluid is a lubricant, and the Quality Control Operator modifies the fluid properties by adjusting the concentrations of additives in the lubricant.

26. The quality control system of claim 13, wherein the fluid is lubricant additive package, and the Quality Control Operator modifies the fluid properties by adjusting the concentrations of components in the additive package.

27. The quality control system of claim 13, wherein the test fluid is a lubricant additive package, and the means for modifying the test fluid modifies the fluid properties by adjusting the concentrations of components in the additive package.

28. The quality control system of claim 13, wherein the first IS signatures and the second IS signatures include principal components.

29. A quality control system controlling properties of a fluid, comprising:
 a) means for obtaining a set of calibration fluids representative of a manufacturing process;
 b) means for performing impedance measurements at on each of the calibration fluids to obtain first impedance spectroscopy (IS) data, wherein the first IS data include data for at least three frequencies;
 c) means for analyzing the first IS data providing first IS signatures indicative of properties for each of the calibration fluids;
 d) means for performing impedance measurements on a test fluid providing second IS data, wherein the second IS data include data for at least three frequencies;
 e) means for analyzing the second IS data providing second IS signatures indicative of properties of the test fluid;
 f) means for comparing the first IS signatures and the second IS signatures providing quality control information relating to the properties of the test fluid; and
 g) means for modifying the properties of the test fluid responsive to the quality control information;
  wherein the means for analyzing the first IS data and the means for analyzing the second IS data employ equivalent circuit modeling, and the first IS signatures and the second IS signatures include at least one of the following: a bulk fluid resistance $R_{fluid}$, a bulk fluid capacitance $C_{fluid}$, a bulk fluid time constant $\tau_{fluid}$, an interface capacitance $C_{dl}$, a charge transfer resistance $R_{ct}$, an interface time constant $\tau_i$, an interface resistance $R_i$, a Constant Phase Element $Q_i$, a Constant Phase Element exponent n, a film time constant $\tau_{film}$, a film resistance $R_{film}$, and a film capacitance $C_{film}$.

30. The quality control system of claim 29, wherein the means for performing impedance measurements includes an IS probe having concentric tubular electrodes.

31. The quality control system of claim 29, wherein the test fluid is a lubricant.

32. The quality control system of claim 29, wherein the test fluid is a lubricant additive package.

33. The quality control system of claim 29, wherein the means for analyzing the first IS data and the means for analyzing the second IS data are a data processing system.

34. The quality control system of claim 33, wherein the data processing system includes a CPU and a memory.

35. The quality control system of claim 29, wherein the means for analyzing the first IS data and the means for analyzing the second IS data employ at least one of the following statistical techniques: Principal Component Analysis, Multivariate Least Squares Regression, Principal Component Regression, Pattern Recognition analysis, Cluster analysis, Neural Net analysis, and Group Methods of Data Handling.

36. The quality control system of claim 35, wherein the first IS signatures and the second IS signatures include principal components.

37. The quality control system of claim 29, wherein the set of calibration fluids include calibration fluids having selected concentrations of at least one additive in a base fluid, and wherein the selected concentrations are representative of desired concentration limits for the at least one additive.

38. The quality control system of claim 37, wherein the base fluid includes at least one component from the following categories: mineral base oil and synthetic base oil.

39. The quality control system of claim 37, wherein the at least one additive includes at least one component selected from the following categories: viscosity modifiers, pour point depressants, stabilizers, seal swell agents, anti-static additives, antioxidants, metal deactivators, anti-foam agents, detergents, dispersants, anti-wear additives, and corrosion inhibitors.

40. The quality control system of claim 29, wherein the means for modifying the test fluid includes at least one of the following: a person, an apparatus, and an automatic system.

41. The quality control system of claim 29, wherein the test fluid is a lubricant, and the means for modifying the test fluid modifies the fluid properties by adjusting the concentrations of additives in the lubricant.

42. A fluid property quality control method, comprising the steps of:
 a) obtaining a set of calibration fluids representative of a first product;
 b) performing impedance measurements on each of the calibration fluids to obtain first impedance spectroscopy (IS) data, wherein the first IS data include data for at least three frequencies;
 c) analyzing the first IS data providing first IS signatures indicative of properties for each of the calibration fluids;
 d) performing impedance measurements on a test fluid providing second IS data, wherein the test fluid is representative of a second product, and wherein the second IS data include data for at least three frequencies;

e) analyzing the second IS data providing second IS signatures indicative of properties of the test fluid;

f) comparing the first IS signatures and the second IS signatures providing quality control information relating to the properties of the test fluid; and g) selectively accepting the second product, responsive to the quality control information;

wherein the step of analyzing the first IS data and the step of analyzing the second IS data include equivalent circuit modeling, and the first IS signatures and the second IS signatures include at least one of the following: a bulk fluid resistance $R_{fluid}$, a bulk fluid capacitance $C_{fluid}$, a bulk fluid time constant $\tau_{fluid}$, an interface capacitance $C_{dl}$, a charge transfer resistance $R_{ct}$, an interface time constant $\tau_i$, an interface resistance $R_i$, a Constant Phase Element $Q_i$, a Constant Phase Element exponent n, a film time constant $\tau_{film}$, a film resistance $R_{film}$, and a film capacitance $C_{film}$.

43. The fluid property quality control method of claim 42, wherein the first product is a genuine product.

44. The fluid property quality control method of claim 43, wherein the second product belongs to one of the following categories: a genuine product and a counterfeit product.

45. The fluid property quality control method of claim 42, wherein the first product is a product of acceptable quality.

46. The fluid property quality control method of claim 45, wherein the second product belongs to one of the following categories: a product of acceptable quality and a product of unacceptable quality.

47. The fluid property quality control method of claim 42, wherein the set of calibration fluids include calibration fluids having selected concentrations of at least one additive in a base fluid, and wherein the selected concentrations are representative of desired concentration limits for the at least one additive.

48. The fluid property quality control method of claim 47, wherein the base fluid includes at least one component from the following categories: mineral base oil and synthetic base oil.

49. The fluid property quality control method of claim 48, wherein the at least one additive includes at least one component selected from the following categories: viscosity modifiers, pour point depressants, stabilizers, seal swell agents, anti-static additives, antioxidants, metal deactivators, anti-foam agents, detergents, dispersants, anti-wear additives, and corrosion inhibitors.

50. The fluid property quality control method of claim 42, wherein the step of analyzing the first IS data and the step of analyzing the second IS data include statistical techniques.

51. The fluid property quality control method of claim 50, wherein the statistical techniques include at least one of the following: Principal Component Analysis, Multivariate Least Squares Regression, Principal Component Regression, Pattern Recognition analysis, Cluster analysis, Neural Net analysis, and Group Methods of Data Handling.

52. The fluid property quality control method of claim 51, wherein the first IS signatures and the second IS signatures include principal components.

53. The fluid property quality control method of claim 42 wherein the frequencies of step a) and step d) each include at least one frequency less than one Hertz, and at least one frequency greater than one Hertz.

54. The fluid property quality control method of claim 42, wherein the test fluid is a lubricant.

55. The fluid property quality control method of claim 42, wherein the test fluid is a lubricant additive package.

* * * * *